United States Patent
Behiels (10) Patent No.: US 7,479,969 B2
(45) Date of Patent: Jan. 20, 2009

(54) GRID DETECTION METHOD

(75) Inventor: Gert Behiels, Edegem (BE)

(73) Assignee: Agfa HealthCare, N.V., Mortsel (BE)

( * ) Notice: Subject to any disclaimer, the term of this patent is extended or adjusted under 35 U.S.C. 154(b) by 384 days.

(21) Appl. No.: 11/350,187

(22) Filed: Feb. 8, 2006

(65) Prior Publication Data

US 2006/0188146 A1    Aug. 24, 2006

Related U.S. Application Data

(60) Provisional application No. 60/662,662, filed on Mar. 17, 2005.

(30) Foreign Application Priority Data

Feb. 24, 2005    (EP) .................................. 05101390

(51) Int. Cl.
G09G 5/00        (2006.01)

(52) U.S. Cl. ........................ 345/629; 345/418; 382/128; 382/132; 382/260; 382/275

(58) Field of Classification Search ................. 345/629; 382/278, 128, 132, 260, 275; 280/310; 702/5; 73/657

See application file for complete search history.

(56) References Cited

U.S. PATENT DOCUMENTS

| 6,269,176 | B1 | 7/2001 | Barski et al. |
| 7,142,705 | B2 * | 11/2006 | Inoue et al. ................. 382/132 |
| 7,282,723 | B2 * | 10/2007 | Schomacker et al. ...... 250/458.1 |
| 2003/0152259 | A1 | 8/2003 | Belykh et al. |

FOREIGN PATENT DOCUMENTS

| EP | 0723762 | 7/1996 |
| EP | 0962888 | 12/1999 |

* cited by examiner

*Primary Examiner*—Kimbinh T Nguyen
(74) *Attorney, Agent, or Firm*—Houston Eliseeva LLP (57) ABSTRACT

Method of detecting an image of a grid in a digital image by extracting a number of features from the digital image and classifying extracted features in a classification algorithm, preferably implemented with support vector machines, which is trained with the same training features extracted from a number of reference images.

22 Claims, 6 Drawing Sheets

GRID DETECTION METHOD

This application claims the benefit of U.S. Provisional Application No. 60/662,662 filed Mar. 17, 2005 and European Patent Application No. 05101390.2 filed Feb. 24, 2005.

FIELD OF THE INVENTION

The present invention relates to a method for detecting grids in a digital image and for obtaining the orientation and frequency of the grid.

BACKGROUND OF THE INVENTION

A commonly used technique to reduce the amount of scattered X-rays in computed radiography, digital radiography as well as classical film-based X-ray systems is the use of anti-scatter grids. These grids are lead foil strips, placed apart at a certain distance in a suitable covering.

There exist different types of anti-scatter grids. In parallel grids, the lead foil strips are parallel, while in honeycomb grids the strips are placed in a honeycomb pattern. The grids are stationary or moving. The use of these grids effectively reduces the radiation scattering but occasionally introduces artifacts such as grid lines into the image.

In a moving system, the motion of the grids removes the grid lines in the image. However, in some circumstances e.g. short exposure time or malfunctioning of the system, the artifacts remain in the image. With stationary grids, the grid lines are almost always visible.

If the image is formed digitally or converted afterwards to a digital image representation, Moiré artefacts may appear when displaying the image at a certain scale. These low frequency Moiré artefacts are mostly disturbing and should be eliminated. Before displaying the image, the grid lines, if present in the image, should be removed. Because the removal algorithms of such grid lines is a time consuming operation, a need exists for a robust method to detect grids in the image so that the processing algorithms for removing grids are only applied when a grid has been used.

SUMMARY OF THE INVENTION

A method of detecting an image of a grid in a digital image includes the steps of: extracting a number of classification features from the digital image; and classifying extracted features in a classification algorithm which is trained with the classification features extracted from a predetermined number of reference images.

The present invention provides a method for detecting grids and retrieving information about these grids. This information can be presented to a grid suppression algorithm.

The method is made robust through the use of several classification features which are extracted from the captured image.

These classification features are presented to a classification algorithm which determines whether or not a grid is present.

If a grid is present, information about the grid is presented. This information includes at least one of the orientation of the grid and the frequencies of the grid patterns which are visible in the image.

An example of a classification feature is the percentage of image regions, perpendicular to the grid direction, which score better for a given measure than regions parallel with the grid.

A suitable measure is the maximum power spectrum magnitude at high frequencies. Regions which have a better measure than an average of the measure in the parallel direction to the grid, are taken regions where the grid is most likely best visible. This average of the parallel direction is just an estimate of the measure if no grid was present in the image.

Another example of a classification feature is the percentage of how many of these image regions have their maximum power spectrum magnitudes located around the same frequency.

A third example of a classification feature is the ratio of the averaged power spectrum magnitude at the most likely frequency to the averaged power spectrum magnitude of the neighbouring frequencies.

A fourth example of a classification feature is the corresponding period of the most likely grid frequency in the image.

The classification algorithm is preferably implemented with support vector machines. The input for training of the algorithm includes an array of the above-mentioned features and the information whether a grid is present.

Support vector machines are for example described in "An introduction to support vector machines and other kernel-based learning methods, N. Cristianini and J. Shawe-Taylor, Cambridge University Press, 2000, ISBN 0 521 78019 5", herein incorporated by reference in its entirety for background information only.

After training, the classification rules are stored.

When a new image is presented to the method for detection, first the above-mentioned features are extracted from the new image, the classification rules are loaded and the decision of the grid's presence is made by the classification algorithm.

The proposed method easily allows the extension of the feature list to make the method more robust if the failure rate with these features is not acceptable.

Further advantages and embodiments of the present invention will become apparent from the following description and drawings.

DETAILED DESCRIPTION OF THE PREFERRED EMBODIMENTS

The input of the method is a digitized radiation image, e.g. a medical image such as an X-ray image. This image is for example obtained by capturing X-rays, generated by an X-ray tube and attenuated by the patient or object to be examined, on a radiation detector such as film or a photostimulable phosphor screen, a CMOS detector or the like.

Although the present invention will be explained with respect to an X-ray image, it is not meant to be limited to this particular type of image.

To reduce the amount of scattering of the X-rays as they pass through the object, an anti-scatter grid is sometimes placed between the object and detector (e.g. the film). This technique is well known and commonly used but can introduce some artefacts in the image. These artefacts especially appear when displaying the image on soft-copy while zooming out the image.

Figure 1:
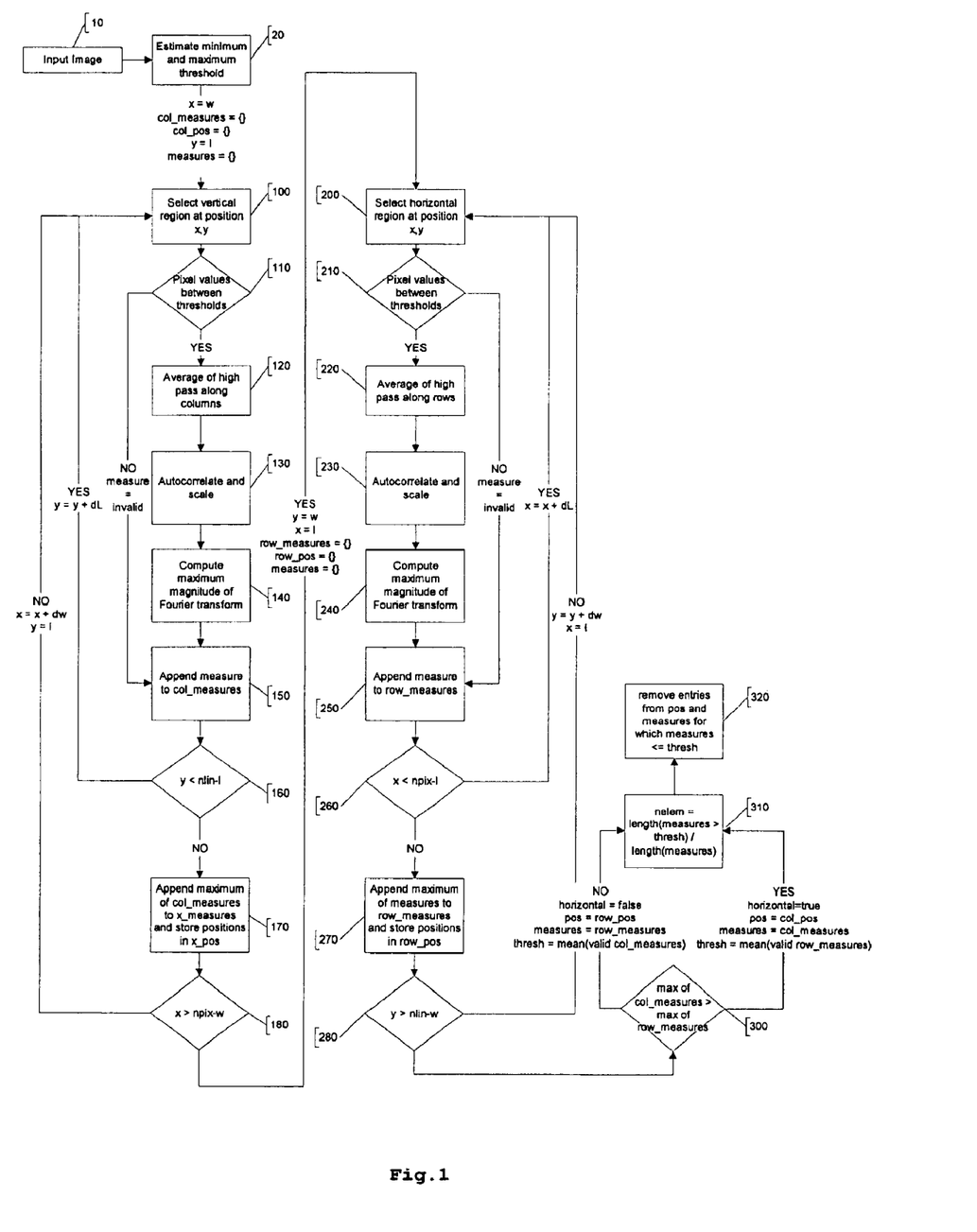
FIG. 1 illustrates an embodiment of an algorithm according to the present invention which determines in which parts of the image the grid is most likely visible and which extracts a first feature and decides in which direction the grid is most likely positioned.

To perform the detection method according the described embodiment of the present invention, the digitized image data is loaded into main memory of a computer or an image processor (Step 10). Before extraction of any features, preferably first a minimum $th_{min}$ and maximum threshold value $th_{max}$ is computed to identify over-exposed and collimation areas. Techniques described in EP 610 605, EP 742 536 and EP 887 769 can be used for this purpose.

Regions with pixel values outside these thresholds can then be discarded as valid input. This is shown in step 110 and step 210.

After this first rough segmentation we try to locate at various positions in both directions the positions at which the grid is most likely visible. We compute a measure for an image region. This measure is computed at different image locations. In a later stage of the algorithm we discard the image locations for which this measure is not better than an estimate of the measure if no grid was present (Step 320).

In the described implementation, this estimate is the average of the measures computed from the perpendicular direction (Step 300-310). The decision of the direction of the grid is done in step 300. In this implementation, we choose the direction for which the measure has the best score.

In the next paragraphs we describe which measure is implemented. Remark that regions which lie in the vertical direction serve to detect grids which lie horizontally. In the current implementation an image region is defined as a rectangle with width W and length L, positioned horizontally or vertically. We do not investigate image regions which lie at the border with width w and length l of the image.

For detection of a horizontal grid, we extract regions for several positions x with width W and length L at different positions y which contain the pixels lying in the rectangle with corner points (x,y) (x+W,y) (x+W,y+L) (x,y+L) for a vertical region (Step 100) and corner points (x,y) (x+L,y) (x+L,y+W) (x,y+W) for a horizontal region (Step 200). If any of the pixel values lies outside the threshold interval of step 20, this region is not used for inspection and an invalid measure is stored in an array of measure for this particular x column (Step 110 and 210). For the different y positions, the best measure is appended to the measures for the horizontal grid direction and the corresponding (x,y) position is saved (Step 170 and Step 270).

The measure at position (x,y) is computed in the following manner. First a high pass filter is used to remove the low frequencies from the region R (Step 120 and 220). Application of a generic simple filter with kernel elements [0.05 0.25-0.6 0.25 0.05] is sufficient but other filters work also. The filtering is done along the length direction of the region. After this high pass filter, the mean of the filtered region is computed along the width of the region (Step 120 and 220).

This removes the noise for a great deal and reduces the impact of the noise at higher frequencies in the Fourier spectrum.

Then we compute the autocorrelation of this mean profile (Step 130 and 230). The autocorrelation enhances the periodic variation in the signal.

The result of the autocorrelation is divided by its maximum value (Step 130 and 230) and the maximum of the magnitude of the Fourier transform of this scaled auto-correlated signal is computed (Step 140 and 240) and stored as measure for position (x,y) for the used direction (Step 150 and 250).

If the measures for both directions are computed, we check if the maximum measure of the horizontal direction is greater than the maximum measure of the vertical direction (Step 300). If this condition is true, we assume that the grid lies horizontally and store the positions and measure for the horizontal direction. We also compute a threshold thresh which represents the mean maximum power spectrum in a direction of the image without grid. This is obtained by averaging the obtained measure for the vertical direction.

If the equation of step 300 does not hold, we assume that the grid lies vertically and store positions and measure for this direction and compute the threshold from the horizontal measures.

The first feature for our classification algorithm now becomes the ratio of the measures in the assumed direction which are larger than the computed threshold over the total number of valid measures in the assumed direction (Step 310). This gives us a number between 0 and 1, which is a measure of confidence if the grid is present in the image or not. However, this feature alone is generally not sufficient enough to determine the presence of the grid.

Figure 4:
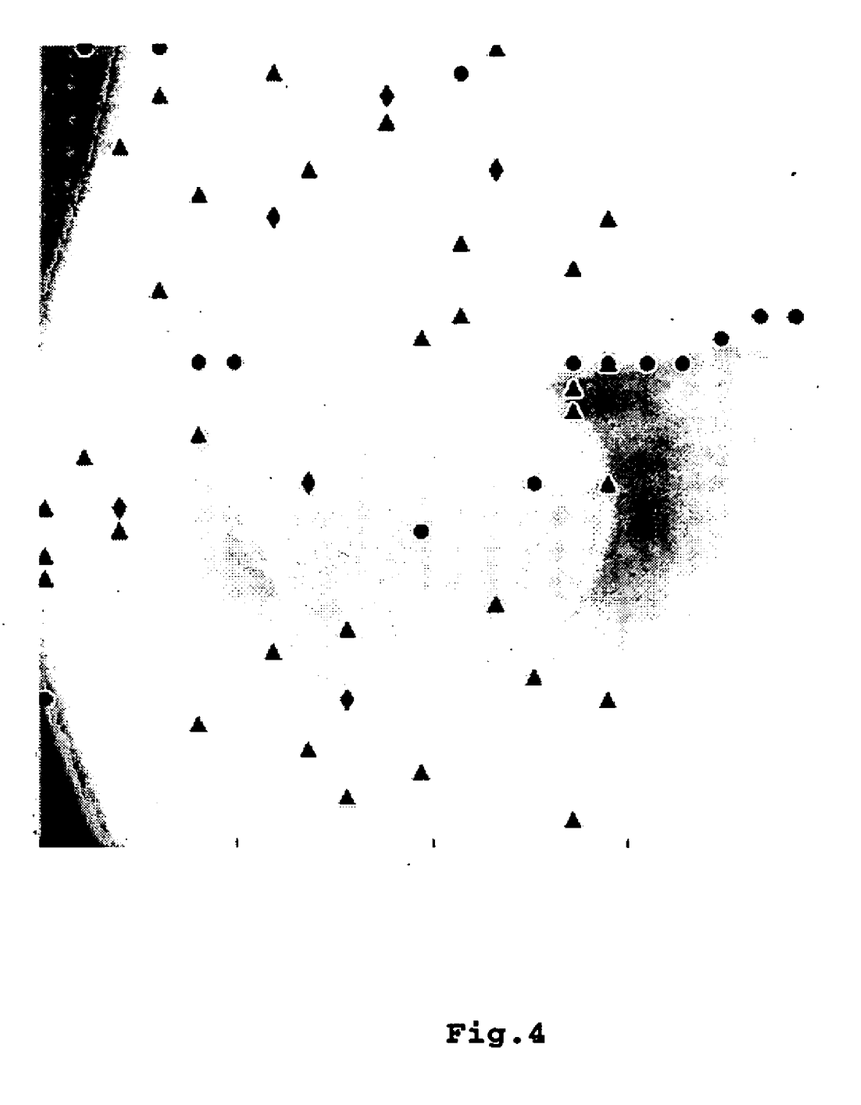
FIG. 4 shows an image with a horizontal grid. The locations where the grid is most visible are indicated with circles. The image locations indicated with diamonds correspond to positions where the maximum magnitude of the Fourier spectrum does not exceed and average maximum magnitude of the Fourier spectrum of image regions in the horizontal direction.

FIG. 4 shows some results on an image with a horizontal grid. The circles represent positions for which the measures are higher than the mean of the measures for the vertical grid. The diamonds are positions for which this comparison does not hold. The black dots are the positions from which the threshold is computed. In this example, the feature nelem of step 310 becomes 0.823. This high value indicates that we are relatively sure there is a horizontal grid present in the image.

Figure 2:
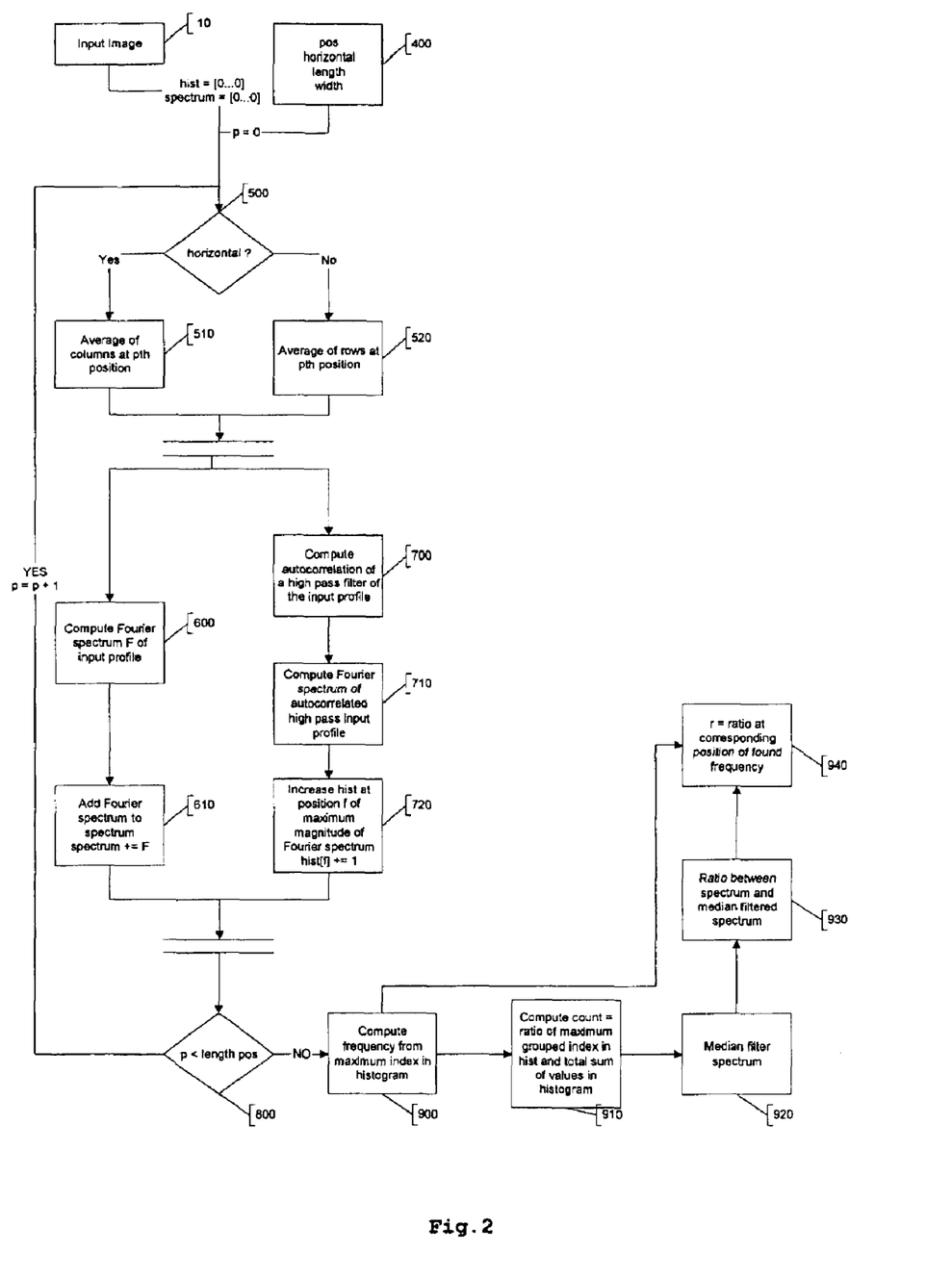
FIG. 2 illustrates an embodiment of an algorithm according to the present invention for the computation of other classification features from the image parts which are determined in the previous step.

After removing the positions for which the measure is lower than the threshold of step 300-310, we continue to step 400 for the extraction of extra features to feed into our classification algorithm.

In step 510 or 520, again we extract regions from the image but now we only do this for the positions of step 320, for which we think the grid is most visible. This region is averaged along the direction of the grid (Step 510 or 520).

For each input position, we accumulate the Fourier spectrum F (step 600 and 610) and increase an entry of a histogram at the relative frequency f for which the amplitude of the Fourier spectrum of the auto-correlated high pass filtered input profile is maximal (steps 700 to 720). The result of both steps for the image of FIG. 4 is displayed in FIG. 5.

In step 900, we search the entry in the histogram with the maximum value. This is the dominant relative frequency φ of the grid which is present in the image. The period defined as $$p = \frac{2}{\varphi}$$

is stored as a classification feature.

In step 910 we accumulate all neighbouring values λ of the frequency φ of step 900 until we reach an entry which is not zero and compute the ratio to the total entries in the histogram.

Figure 5:
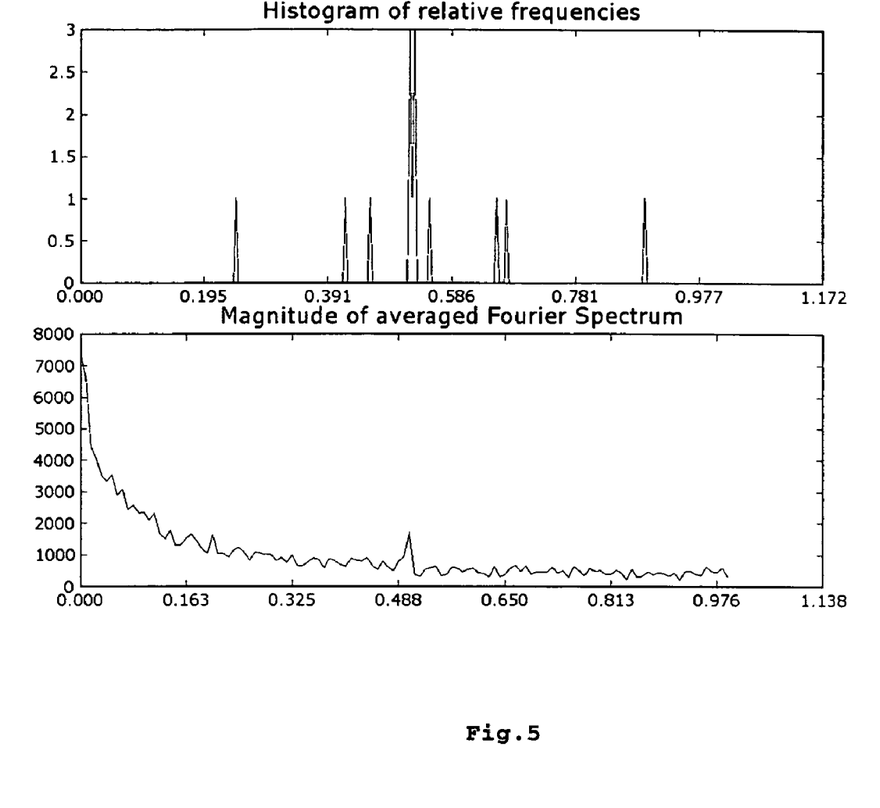
FIG. 5 shows a histogram of the relative frequencies at the locations with the circles in FIG. 4 and the average magnitude of the Fourier spectrum at these locations.

In the example of FIG. 5, we obtain a value of 7 out of 14 entries. The count feature for this example is 0.5.

In step 920, we also perform a median filter on the averaged Fourier spectrum and compute the ratio to the original spectrum (Step 930). In Step 940, we search the maximum ratio at the relative frequencies λ which contributed to the count feature in step 910.

Figure 6:
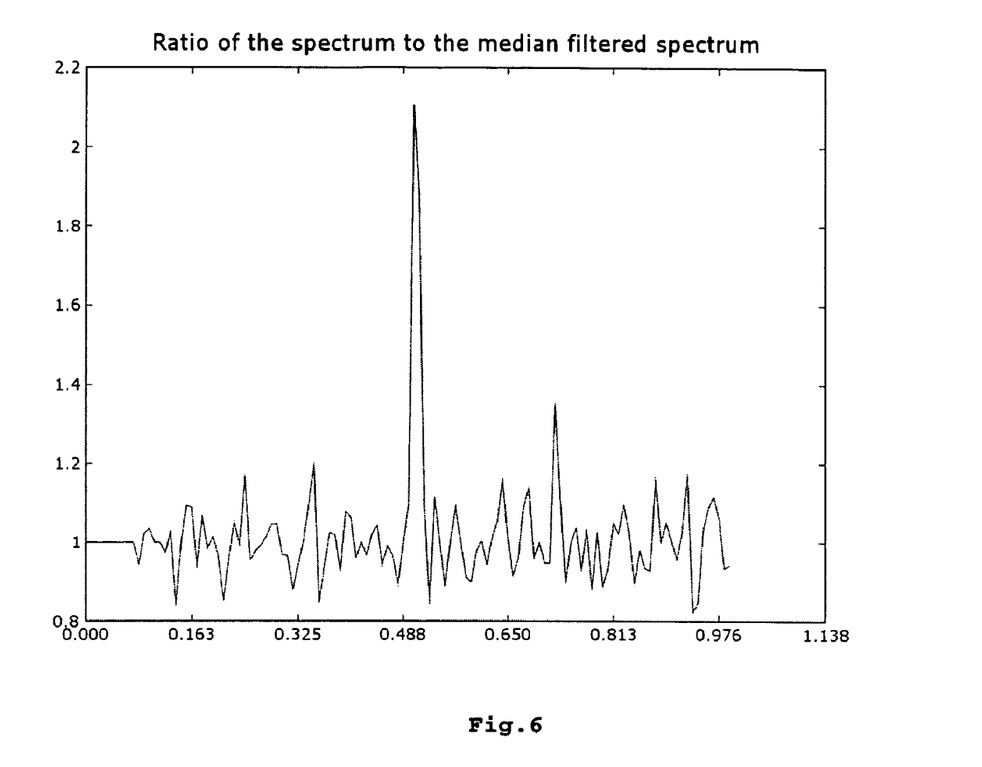
FIG. 6 shows the ratio of the average magnitude of the Fourier spectrum to a median filtered version of this average magnitude.

FIG. 6 shows the ratio of the spectrum and the median filtered spectrum. In our example, the last feature r becomes 2.10.

As an additional step, we can also compute the harmonics or corresponding low frequencies at which the grid manifests itself in the image. First of all, we have the ground frequency φ obtained in the algorithm depicted in FIG. 2 and a corresponding ratio entry. From this value, we compute a new threshold for the ratio.

$$th = \max(th_{min}, \min(th_{max}, (r-1)*perc+1))$$

$th_{min}$ is the predefined minimum value for the ratio, $th_{max}$ is the predefined maximum value for the ratio, perc is a predefined value between 0 and 1.

We define new scales and intervals on which we find new relative frequencies for which the maximum value of the ratio in the defined intervals are greater than th. If for a given scale and range, the following equation holds, the new relative frequency scale*f is added to frequencies we want to suppress the frequency γ satisfying the following conditions:

$$ratio[\gamma] = \max(ratio[scale*\phi*L-range, scale*\phi*L+range]) \; ratio[\gamma] > th$$

In some conditions, the grid manifests itself in a lower frequency around the relative frequency (1−φ). We also want to suppress the following low frequencies h $$ratio[\eta] = \max(ratio[scale*(1-\phi)*L-range, scale*(1-\phi)*L+range]) \; ratio[\eta] > th$$

with scale equal to 1 or 2.

Figure 3:
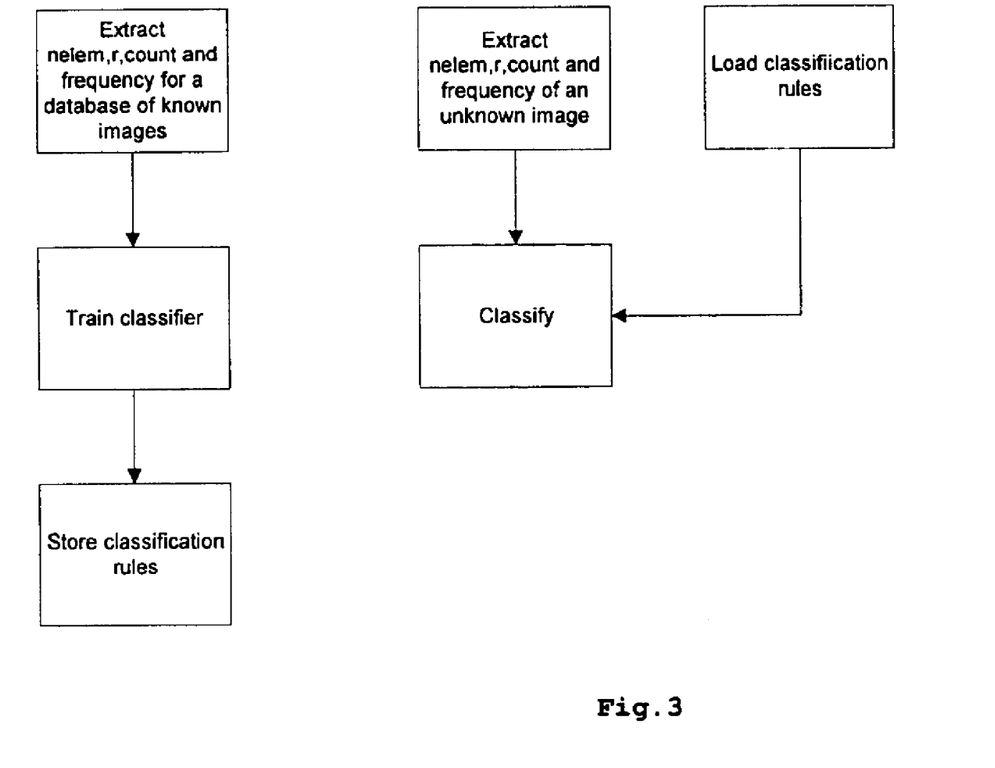
FIG. 3 shows a flowchart regarding the training and use of the classification algorithm.

Having defined all these features, we are now able to train our classification algorithm.

From a number of images (also referred to as reference images) stored in advance in a database, we extract the above mentioned features and supply them as input together with the information which of the images contain grids.

The choice of the classification algorithm is free.

We use cross validation against reference images from our database to choose the best classification parameters for a support vector machine implementation preferably with linear basis functions because of the simplicity. However, other basis functions such as radial basis functions are also applicable.

The invention claimed is:

1. A method of detecting a presence of an image of a linear grid parallel to one of the edges of an image represented by a digital image representation, comprising:
   computing predefined measures for different image locations in said image in a computer,
   determining an assumed direction of said grid by comparing said predefined measures for a first direction and a second direction,
   computing a confidence feature by steps including:
      deducing a reference value from the predefined measures in a direction perpendicular to said assumed direction,
      calculating said confidence feature as a ratio of a number of the predefined measures in the assumed grid direction which are larger than said reference value to the total number of predefined measures in the assumed direction,
   detecting a presence of said grid from the predefined measures and said confidence feature.

2. A method according to claim 1 wherein said assumed direction of the grid is determined by steps including:
   computing the maximum of the predefined measures for said first direction and said second direction, and
   if a maximum of the predefined measures for said first direction is greater than a maximum of the predefined measures for said second direction, assuming that said first direction is the grid direction, else assuming that said first direction is the grid direction.

3. A method according to claim 1 wherein said predefined measures are a maximum of a magnitude of a Fourier spectrum of a high-pass image region.

4. A method according to claim 1 wherein said predefined measures are a maximum of an averaged high-pass filtered image region.

5. A method according to claim 1 wherein said predefined measures are a maximum of an averaged high-pass scaled auto-correlated pixel values in an image region.

6. A method according to claim 1 wherein said reference value of the predefined measures for an image in which no grid image was present is equal to an average of predefined measures computed for a direction perpendicular to the assumed grid direction.

7. A method according to claim 1 wherein regions in said digital image for which said predefined measures perform worse than an estimate of said predefined measure are discarded.

8. A method according to claim 1 wherein parts of said digital image representing collimated areas are discarded.

9. A method according to claim 1 wherein parts of said digital image representing overexposed areas are discarded.

10. A method of detecting a presence of an image of a linear grid parallel to one of the edges of an image represented by a digital image representation comprising the steps of
    training a classification algorithm with classification parameters comprising predefined measures and at least one confidence feature extracted from a number of reference images in a computer,
    extracting said classification parameters from said digital image,
    classifying said classification parameters from said digital image in the trained classification algorithm,
       wherein said classification parameters comprise said measures and said at least one confidence features, said at least one confidence feature is computed by steps including:
       deducing a reference value from the predefined measures in a direction perpendicular to assumed direction of the grid,
       calculating said at least one confidence feature as a ratio of a number of the predefined measures in the assumed grid direction which are larger than said reference value to the total number of predefined measures in the assumed direction.

11. A method according to claim 10 wherein one of said at least one confidence features is a ratio of a number of locations where predefined measures are better than an estimate to a number where said predefined measure are worse than said estimate.

12. A method according to claim 10 wherein said classification algorithm is implemented with a support vector machine.

13. A method according to claim 12 wherein a kernel function of said support vector machine is a linear basis function.

14. A method according to claim 10 wherein optimal values of classification parameters of said classification algorithm are obtained by optimizing said classification parameters by cross-validation against said classification parameters extracted from said reference images.

15. A method according to claim 10 wherein one of said features is the period of said grid.

16. A method according to claim 15 wherein said period of the grid is determined as a period where a corresponding entry in a histogram of frequencies at a maximum magnitudes of a Fourier spectra at different image regions where said measure is better than said estimate, is maximal.

17. A method according to claim 10 wherein one of said features is the ratio of the magnitude of the average Fourier spectrum at different image positions at the grid frequency to the magnitude of the low pass filtered averaged Fourier spectrum.

18. A method according to claim 10 wherein one of said at least one confidence features is the ratio of a number of image positions where a maximum magnitude of a Fourier spectrum is located at a grid frequency and a number of image positions where a maximum frequency of the Fourier spectrum is not located at the grid frequency.

19. A method according to claim 18 wherein the Fourier spectrum of an image region is computed after averaging the image region along the grid direction.

20. A method according to claim 18 wherein the Fourier spectrum of an image region is computed after high-pass filtering the averaged image region.

21. A method according to claim 20 wherein the Fourier spectrum of an image region is computed after auto correlating a high-pass filtered averaged image region.

22. A method according to claim 10, wherein said digital image represents a medical image and said grid is an anti-scatter grid.

* * * * *